US010991098B1

(12) United States Patent
Hänselmann et al.

(10) Patent No.: US 10,991,098 B1
(45) Date of Patent: Apr. 27, 2021

(54) METHODS FOR AUTOMATED CHROMOSOME ANALYSIS

(71) Applicant: MetaSystems Hard & Software GmbH, Altlussheim (DE)

(72) Inventors: Siegfried Hänselmann, Heidelberg (DE); Thomas Lörch, Reilingen (DE)

(73) Assignee: MetaSystems Hard & Software GmbH, Altlussheim (DE)

( * ) Notice: Subject to any disclaimer, the term of this patent is extended or adjusted under 35 U.S.C. 154(b) by 0 days.

(21) Appl. No.: 17/074,440

(22) Filed: Oct. 19, 2020

Related U.S. Application Data

(60) Provisional application No. 62/916,766, filed on Oct. 17, 2019.

(51) Int. Cl.
*G06K 9/00* (2006.01)
*C40B 30/04* (2006.01)
*G06T 7/00* (2017.01)
*G06T 7/62* (2017.01)
*G06T 7/155* (2017.01)

(52) U.S. Cl.
CPC ............ *G06T 7/0012* (2013.01); *G06T 7/155* (2017.01); *G06T 7/62* (2017.01); *G06T 2207/30024* (2013.01)

(58) Field of Classification Search
USPC ....... 382/100, 103, 128–134, 154, 156, 162, 382/168, 181, 190, 199, 209, 224, 232, 382/254, 274, 276, 286, 305, 321; 1/1; 506/8, 9, 17
See application file for complete search history.

(56) References Cited

U.S. PATENT DOCUMENTS

| | | | |
|---|---|---|---|
| 10,621,474 B2* | 4/2020 | Sharma | G06T 7/0012 |
| 2005/0265588 A1* | 12/2005 | Gholap | G06K 9/00127 |
| | | | 382/128 |
| 2009/0118132 A1* | 5/2009 | Haferlach | C12Q 1/6886 |
| | | | 506/8 |
| 2013/0216118 A1* | 8/2013 | Rogan | C12Q 1/6883 |
| | | | 382/133 |
| 2014/0073520 A1* | 3/2014 | Cai | C12Q 1/6841 |
| | | | 506/9 |
| 2020/0050831 A1* | 2/2020 | Rogan | G06K 9/00134 |

FOREIGN PATENT DOCUMENTS

CN 109344874 A 2/2019

OTHER PUBLICATIONS

Swati et al., "Siamese Networks for Chromosome Classification," 2017 IEEE International Conference on Computer Vision Workshops (ICCVW), Venice, 2017, pp. 72-81, doi: 10.1109/ICCVW.2017.17.

Abid, F. et al., "A survey of neural network based automated systems for human chromosome classification", Artificial Intelligence Review, Jan. 2018, 49(1), pp. 41-56 (published online Sep. 17, 2016), DOI: 10.1007/s10462-016-9515-5.

(Continued)

*Primary Examiner* — Seyed H Azarian
(74) *Attorney, Agent, or Firm* — Verrill Dana, LLP

(57) ABSTRACT

An automated or semi-automated process to prepare karyotypes from metaphase cell images with improved accuracy involves the use of deep convoluted neural networks for both chromosome segmentation and chromosome classification.

24 Claims, 13 Drawing Sheets

(56) References Cited

OTHER PUBLICATIONS

Jennings, A.M. et al., "A neural network approach to automatic chromosome classification", Phys. Med. Biol., (1993), vol. 38, pp. 959-970.
Sharma, M. et al., "Crowdsourcing for Chromosome Segmentation and Deep Classification", 2017 IEEE Conference on Computer Vision and Pattern Recognition Workshops (CVPRW), Honolulu, HI, 2017, pp. 786-793, doi: 10.1109/CVPRW.2017.109.
Falk, T. et al., "U-Net: deep learning for cell counting, detection, and morphometry", Nature Methods, Jan. 2019, vol. 16, No. 1, pp. 67-70.
Zhang, W. et al., "Chromosome Classification with Convolutional Neural Network based Deep Learning", 2018 11th International Congress on Image and Signal Processing, Biomedical Engineering and Informatics (CISP-BMEI), IEEE, Oct. 13, 2018, pp. 1-5.
Qin, Y. et al., "Varifocal-Net: A Chromosome Classification Approach Using Deep Convolutional Networks", ARIXV.ORG, Cornell University Library, Oct. 14, 2018.

\* cited by examiner

Train 1st DNN for segmentation of
metaphase images into objects
using image pairs
(orig. metaphase image + target map)

Target map pixels classified as:
    1) background/artefact area
    2) chromosome area
    3) overlap area
    4) chromosome contour Train 2nd DNN to classify separated objects as:

1) debris
    2) debris cluster (chromosome(s) + debris)
    3) single chromosome
    4) chromosome cluster
    5) chromosome overlap

Fig. 1B

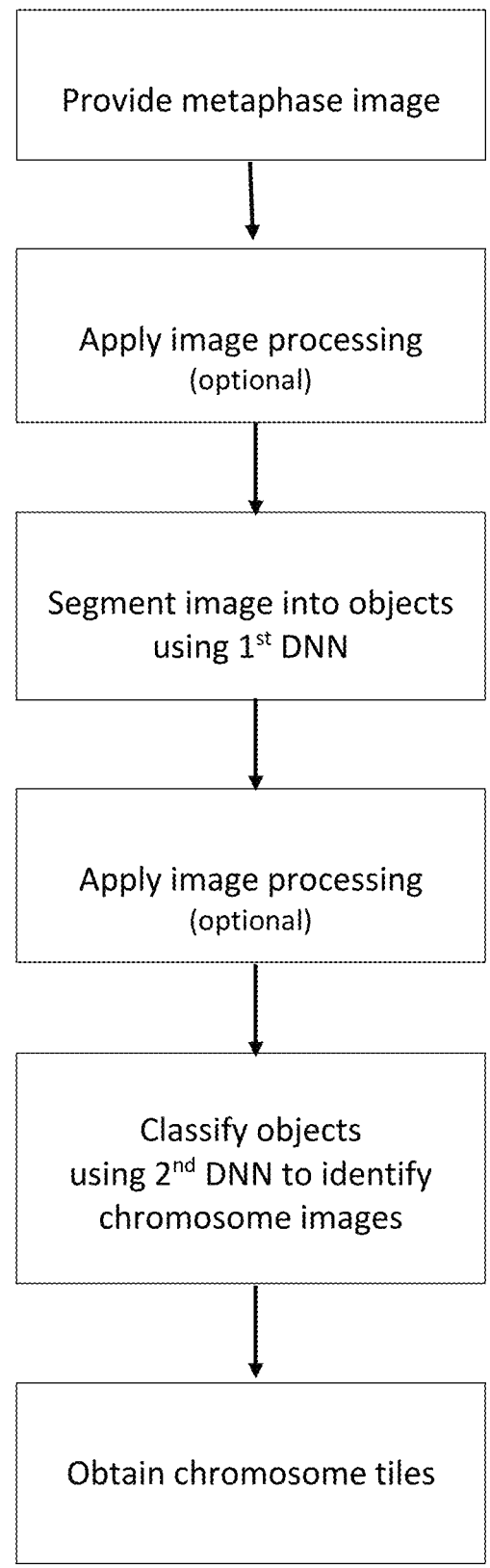

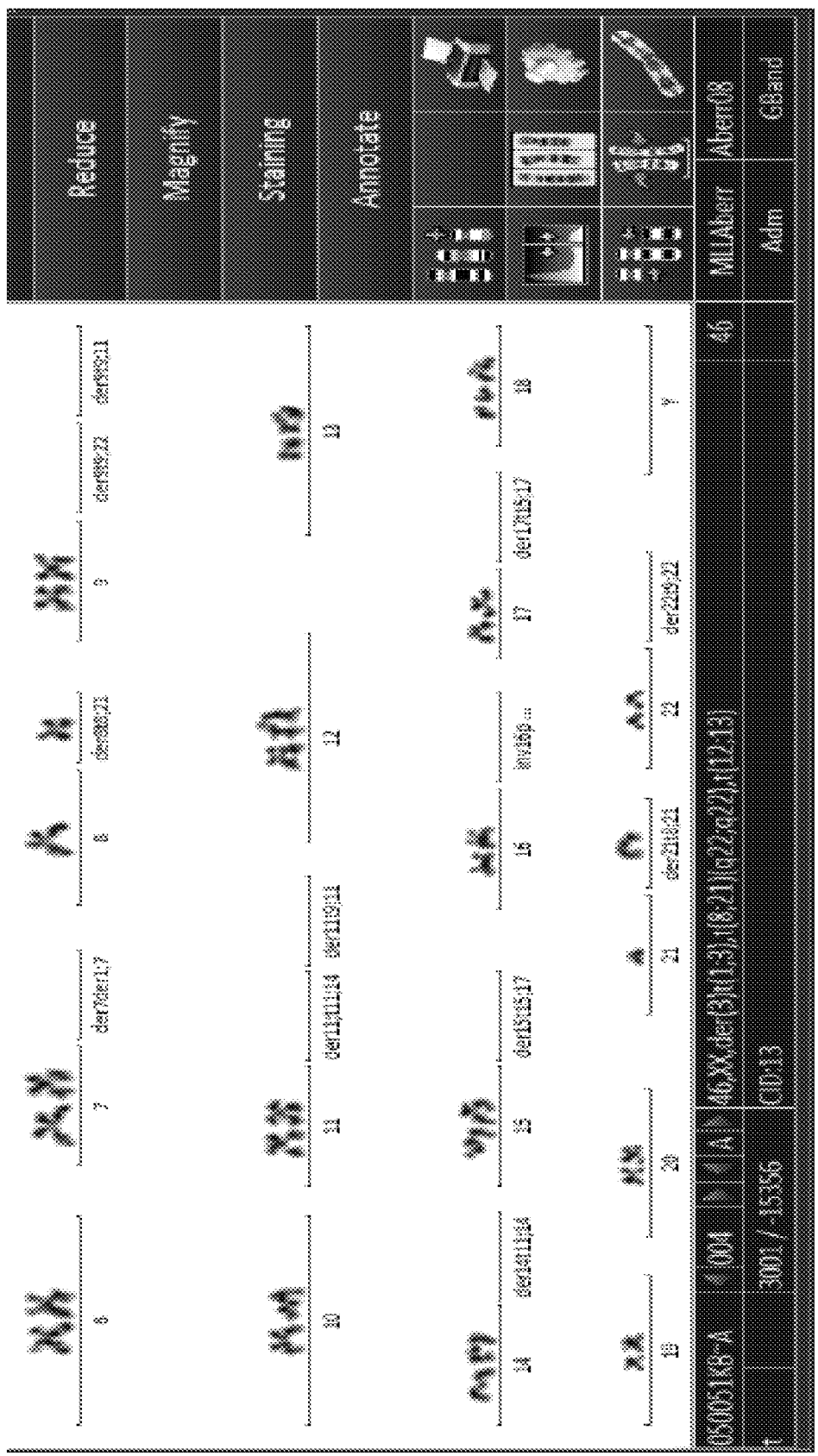
Fig. 4A – continued

METHODS FOR AUTOMATED CHROMOSOME ANALYSIS

CROSS-REFERENCE TO RELATED APPLICATIONS

This application claims the priority of U.S. Provisional Application No. 62/916,766 filed 17 Oct. 2019 and entitled "Methods for Automated Chromosome analysis", the whole of which is hereby incorporated by reference.

BACKGROUND

Chromosome analysis has been the gold standard in genetic diagnosis for decades. Although molecular methods have become important, they do not provide the "global" information on the genetic status of an organism, an organ, or a biopsy. Karyotyping thus remains a procedure that is performed regularly, either as an initial test, e.g., in leukemia diagnostics, or to confirm findings generated through molecular methods (such as after a positive result of a non-invasive, blood based prenatal molecular test).

There is a lot of interest in streamlining the diagnostic procedure of karyotyping, and particularly in speeding up the chromosome classification by the human expert. Moreover, experienced cytogenetic technologists are becoming increasingly difficult to find.

Although various efforts have been made to automate the classification of chromosomes, the reliability of the results have not been satisfactory. The limitations of the results in leukemia diagnosis for instance, can be caused by the poor banding quality of the chromosomes prepared from bone marrow samples. Some protocols require significant effort to prepare or modify chromosome images, such as chromosome straightening as suggested by Sharma et al. Typical error rates of automatic chromosome recognition per cell, based on feature analysis such as intensity profiles along the chromosome axis, are on the order of 65%, meaning that a large fraction need to be manually corrected. Thus, there is a need for more accurate methods for automated chromosome analysis.

SUMMARY

An objective of the present technology is to increase the classification accuracy in karyotyping by applying deep convolutional neural network models to metaphase or other chromosome images so as to reduce or eliminate the need for preparatory processing steps and user intervention.

Another objective of the present technology is to provide a precise estimate of the orientation of the main axis of each chromosome in a karyotype analysis. For karyotype analysis, the chromosomes are aligned vertically and pairwise in a karyogram to facilitate comparison of the banding patterns. Rotating the chromosomes manually to a vertical orientation with the short chromosome arm oriented upwards and the long chromosome arm downwards represents approximately the same amount of time as recognizing the class of a chromosome. Automating both the class assignment and the orientation is therefore highly desirable.

To achieve both objectives, the inventors designed a deep convolutional neural network (DNN) that accepts individual chromosomes and reliably assigns the chromosome class and simultaneously provides the orientation angle of the chromosome. The inventors also designed other DNNs which can be used to automate segmentation of chromosome images from an image of a metaphase cell. The result is a vastly more efficient process from metaphase cell image to karyogram, which is fully automated or requires greatly reduced user interaction.

The present technology can be further summarized in the following listing of features.

1. A method to aid in classifying metaphase chromosomes of a cell, the method comprising the steps of:
   (a) providing a digital image of a metaphase cell;
   (b) segmenting the image into objects, whereby digital images of metaphase chromosomes of the cell are obtained;
   (c) analyzing each chromosome image using a classifying pre-trained deep convolutional neural network (DNN) comprising a first output layer for chromosome classification and a second output layer for chromosome rotation, thereby obtaining for each chromosome (i) a probability vector for use in assigning a class of the chromosome and (ii) a rotation angle of the chromosome in said digital image of the metaphase cell.

2. The method of feature 1, wherein the probability vectors of all chromosomes in the image of the metaphase cell are represented as a probability matrix.

3. The method of feature 1 or feature 2, wherein all chromosomes of the metaphase cell are represented in the digital image of the metaphase cell.

4. The method of feature 2 or feature 3, further comprising:
   (d) assigning the chromosome image with the highest assignment probability to the class predicted for that probability, and
   (e) repeating step (d) with the chromosome image having the next highest assignment probability, until all chromosome images from the image of the metaphase cell have been assigned, with the proviso that once an expected total number of chromosomes for a given class has been reached, assignment probabilities for that class are set to zero or can be recalculated for all remaining unclassified chromosome images.

5. The method of feature 4, wherein chromosome images having an assignment probability below a user-defined threshold are not assigned automatically, but remain unclassified.

6. The method of any of the preceding features, wherein the metaphase cell was pre-treated to reveal one or more nucleic acid sequences or one or more bands or positions on the metaphase chromosomes, and the DNN was pre-trained using the same pre-treatment.

7. The method of feature 6, wherein the pre-treatment comprises performing fluorescence in situ hybridization (FISH), or a variant thereof using non-fluorescent labels.

8. The method of any of the preceding features, wherein the metaphase cell is a eukaryotic cell, such as a cell from a plant, animal, mammal, or human.

9. The method of any of the preceding features, further comprising processing the digital image of the metaphase cell, and/or the digital image of one or more metaphase chromosomes, using an automated or interactive image processing method.

10. The method of feature 9, wherein the image processing method is selected from the group consisting of convolution, concatenation, dropout, average pooling, thresholding, applying a sharpening or averaging filter, gray level transformation, normalization, area normalization, rotation, flipping, addition of random noise, and threshold-based segmentation.

11. The method of any of the preceding features which detects additional or missing chromosomes of a class.

12. The method of any of the preceding features which detects structural aberrations and/or debris.

13. The method of feature 12, wherein the structural aberration is selected from the group consisting of dicentric chromosomes, ring chromosomes. Philadelphia chromosome, and other chromosomal aberrations.

14. The method of feature 13, wherein the structural aberration is selected from the group consisting of t(9; 22)(q34; q11), t(15; 17)(q24; q21), t(11; 14)(q13; q32), der(1; 7)(q10; p10), inv(3)(q21q26), inv(16)(p13q22), t(9; 11)(p21; q23), t(8; 21)(q22; q22), del(5)(q14q34), and del(5)(q21q34).

15. The method of any of the preceding features, wherein step (a) comprises analyzing a plurality of images of metaphase cells and rejecting or flagging images of metaphase cells containing overlapping chromosomes.

16. The method of any of the preceding features, wherein step (b) comprises rejecting or flagging images of metaphase cells containing fewer metaphase chromosomes than expected.

17. The method of any of the preceding features, wherein step (b) comprises:
    (i) optionally applying one or more image processing steps to the digital image of the metaphase cell;
    (ii) segmenting the digital image of the metaphase cell into object images using a pre-trained first segmenting DNN;
    (iii) optionally applying one or more image processing steps to the object images obtained from (ii);
    (iv) classifying the objects obtained in (ii) or (iii) using a pre-trained second segmenting DNN, thereby identifying objects that comprise metaphase chromosome images; and
    (v) preparing digital images of the metaphase chromosomes from the metaphase chromosome images obtained in (iii), wherein the prepared digital images have equal numbers of pixels and equal aspect ratios and are suitable as input for the classifying DNN of step (c).

18. The method of feature 17, wherein the image processing method of step (i) and/or step (iii) is selected from the group consisting of convolution, concatenation, dropout, average pooling, thresholding, applying a sharpening or averaging filter, gray level transformation, normalization, area normalization, rotation, flipping, addition of random noise, and threshold-based segmentation.

19. The method of feature 17 or feature 18, wherein the first segmenting DNN was pre-trained to classify pixels of the digital image of the metaphase cell as background or artefact area, chromosome area, chromosome overlap area, or chromosome contour.

20. The method of feature 17 or feature 18, wherein the second segmenting DNN was pre-trained to classify objects from step (ii) or (iii) as containing debris, debris+chromosome, single chromosome, chromosome cluster, or overlapped chromosomes.

21. The method of feature 20, further comprising performing the method of feature 19.

22. The method of any of the preceding features, further comprising, prior to step (a), identifying metaphase cells in a plurality of cells on a microscope slide.

23. The method of any of the preceding features, further comprising preparing a karyogram using the classified metaphase chromosome images.

24. A method of training a DNN for use in classifying metaphase chromosomes, the method comprising the steps of:
    (a) providing a plurality of sets of training images of metaphase chromosomes, the images of each set containing pre-classified images of all metaphase chromosomes from a metaphase cell of a selected cell type;
    (b) providing a DNN comprising a first output layer for chromosome classification and a second output layer for determining chromosome rotation; and
    (c) training the DNN with the plurality of sets of training images of metaphase chromosomes.

25. The method of feature 24, wherein the sets of training images are karyograms, and at least 10,000, at least 50,000, or at least 100,000 karyograms are used to train the DNN.

26. A method of training a DNN for use in segmenting metaphase chromosomes in an image of a metaphase cell, the method comprising the steps of:
    (a) providing a plurality of pairs of unsegmented images of metaphase cells and corresponding images pre-segmented into objects suspected of containing metaphase chromosomes;
    (b) providing a DNN capable of classifying pixels in the images as corresponding to background or artefact area, chromosome area, chromosome overlap area, or chromosome contour; and
    (c) training the DNN with the plurality of pairs of images of metaphase cells.

27. The method of feature 26, wherein at least 10,000, at least 50,000, or at least 100,000 pairs of training images of unsegmented/segmented metaphase cells are used to train the DNN.

28. A method of training a DNN for use in segmenting metaphase chromosomes in an image of a metaphase cell, the method comprising the steps of:
    (a) providing a plurality of pairs of metaphase cells pre-segmented into objects suspected of containing metaphase chromosomes and images of objects pre-confirmed as containing metaphase chromosomes;
    (b) providing a DNN capable of classifying objects in the images as containing debris, debris+chromosome, single chromosome, chromosome cluster, or overlapped chromosomes; and
    (c) training the DNN with the plurality of pairs of images.

29. The method of feature 28, wherein at least 10,000, at least 50,000, or at least 100,000 pairs of training images are used to train the DNN.

30. A system for automated or semi-automated chromosome classification, the system comprising:
    (i) a light microscope with a digital imaging device, wherein the microscope optionally comprises a motorized focus and scanning stage;
    (ii) a computer configured to control the motorized microscope and digital imaging device, and to capture images, and
    (iii) software configured to perform the method of any of features 1-23 or any combination thereof.

BRIEF DESCRIPTION OF THE DRAWINGS

FIGS. 1A-1F are flow diagrams depicting features of the present technology.

FIG. 1A depicts the overall process from identification of metaphase cells to karyogram preparation, including the deep learning based segregation of individual chromosome images and chromosome classification, including identification of aberrant chromosomes.

FIG. 1B depicts classifications made by two deep convolutional neural networks (DNNs) used in chromosome segregation from an image of a metaphase cell. The first DNN segments the metaphase cell image into images of individual objects, and the second DNN classifies the objects and identifies which correspond to individual chromosomes.

FIG. 1C depicts an overall process of chromosome segregation using the DNNs shown in FIG. 1B. The end product of this process is a series of chromosome "tiles" or images having the same number of pixels and aspect ratio, which can serve as input for a chromosome classifying DNN.

FIG. 1D depicts an image processing protocol which can be employed at one or more different stages of chromosome segmentation. Other image processing techniques also can be applied.

FIG. 1E depicts a chromosome classifier training protocol.

FIG. 1F depicts a process of classifying chromosome images using a pre-trained DNN and probability vector analysis to produce a karyogram.

FIG. 2A shows the original light microscope image of the metaphase chromosomes.

FIG. 2B shows the image after threshold based segmentation (full chromosome field at left after image processing, segmented chromosome images towards the right). FIG. 2C shows the result of an interactive, 39-step image processing process, with borders of segmented chromosome images outlined. FIG. 2D shows the result of chromosome segmentation performed by a first trained DNN that indicates chromosome contours.

FIG. 3A shows the raw microscope image, and FIG. 3B shows the classification of chromosome area vs. overlap area obtained from the DNN.

DETAILED DESCRIPTION

The present technology provides automated chromosome identification and classification using a collection of deep convolutional neural networks (DNNs) which reduces or eliminates the need for preparatory processing steps and user intervention and produces improved accuracy compared to previous methods. Key aspects of the methods include the use of DNNs for segmenting chromosome images from an image of a metaphase cell and use of DNNs for identifying chromosome class, including aberrant classes, and chromosome rotation angle. The methods can optionally be supplemented by user managed image refinement to further improve accuracy and/or image quality.

Figure 1A:
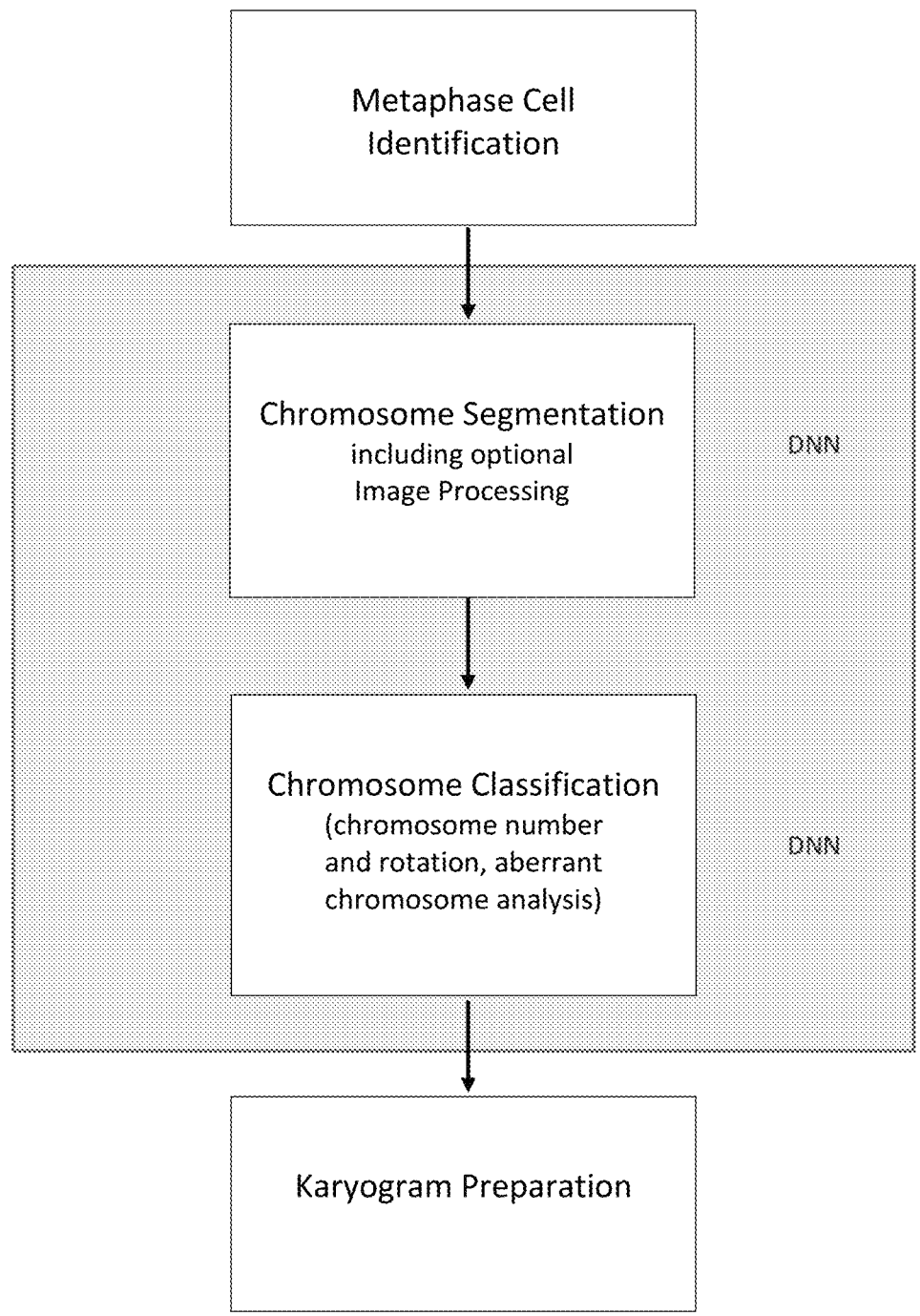

FIG. 1A presents an overview of the methodology. Using standard techniques, cells are cultured in the presence of an inhibitor of mitosis, such a vinblastine, causing an accumulation of cells arrested at metaphase. The cells are deposited on glass microscope slides and stained using standard methods, such as Giemsa staining, which renders the chromosomes and their banding patterns visible in the light microscope. Other techniques can be used to visualize chromosomes, portions of chromosomes, including individual bands or the location of genes, nucleic acid sequences, or chromosomal proteins. For example, oligonucleotide probes (with fluorescent or non-fluorescent labels) can be used to localize genomic nucleic acid sequences, or antibodies can be used to visualize proteins. Metaphase cells on such stained slides are identified either by a human observer at the microscope or with the aid of an automated metaphase cell finder. Any eukaryotic cell type can be the subject of the chromosome analysis, including plant cells, animal cells, mammalian cells, and human cells. The cell can also be a cell representative of a medical condition, such as a type of cancer, or a known or suspected genetic condition, such as an inherited genetic disorder.

Once digital images of one or more metaphase cells have been obtained, certain optional image processing steps can be performed with the goals of simplifying and improving the accuracy of chromosome identification in the metaphase cell image. Any image processing protocol, either automated or interactive, can be used as desired or deemed helpful by the user, at any stage in the methods of the present technology. Individual chromosome images are segmented in the metaphase cell image with the use of a first segmenting DNN. Individual object images are then classified using a second segmenting DNN, and those objects representing single chromosomes are presented to a chromosome classifier DNN, which determines the probability of each chromosome corresponding to each possible class expected for the eukaryotic cell under consideration, optionally including classes of known aberrant chromosomes for the type of cell, or for known symptoms or medical conditions of the tissue or organism from which the cell was obtained. The final outcome of the process is a karyogram prepared either in automated fashion or by a human operator using the classified chromosome images.

Acquiring digital images of metaphase cells by traditional methods is performed by putting the slide containing the cytogenetic preparation under a manual microscope. Suitable cells are then manually located, focused, and captured by means of a camera connected to the microscope. This procedure can be quite tedious, particularly in situations where metaphase cells are scarce, which tends to the case in preparations from cancer patients, e.g., leukemia patients.

A much more efficient method to acquire metaphase cells is by employing an automated slide scanning platform such as the METAFER system (MetaSystems Hard & Software GmbH, Altlussheim, Germany). METAFER consists of a motorized microscope (Carl Zeiss Axiolmager.Z2), a motorized scanning stage (Marzhsuser), a digital camera (MetaSystems), a personal computer for system control and image analysis, and a slide loader robot with several magazines. Specimens are usually put on standard glass slides of 1" by 3". Typically, 5 slides are held in one slide holder. Each magazine holds 16 slide holders. Up to 10 magazines are supported, enabling unattended scanning of up to 800 slides. When a slide holder is loaded from the magazine, it is first transported to a bar code reader where the holder barcode as well as the individual slide barcodes are read. The slide barcodes refer to data files that define the scanning action to be taken for each individual slide. Next, the slide holder is put on the scanning stage and the scan starts.

METAFER can also be run without a slide feeder system. In this case, the slide holder is put manually on the scanning stage, and the barcode is read using a handheld scanner or is imaged through a low power microscope objective and analyzed by the METAFER software. Manual set up of the scan parameters is possible as an alternative to barcodes.

The first step of the scan is automatic light adjustment to assure good contrast. This is followed by a grid focus analysis. At a predefined number of grid positions within the scan area, the plane of best focus is automatically detected, and an interpolated focus surface of the sample is calculated. During the actual scan, the system will automatically follow this predetermined focus surface; it will analyze each captured field on the fly and will detect metaphase cells, whose thumbnail images and x,y,z coordinates are stored. The scan continues until a preset number of metaphases have been detected or until the scan area has been completely scanned.

All these steps are typically performed using a 10× objective lens which provides sufficient resolution to reliably detect metaphase cells.

For chromosome analysis, high quality images of the metaphase cells are required. To achieve this, the METAFER system will, in a next step, change the objective lens and apply immersion oil if necessary. Based on the previously generated position list, high magnification images are then captured. As the initial coarse grid focus is not sufficient to assure perfect focusing of high aperture lenses with their reduced depth of field (compared to the relatively high depth of field of the low magnification, low numerical aperture lens used for the pre-scan), each individual high magnification image needs to be refocused. Individual images are taken for each detected or pre-selected metaphase with the individual metaphase cell centered in the field of view of the camera. Digital metaphase images are then stored for subsequent chromosome analysis and karyotyping.

Figure 1D:
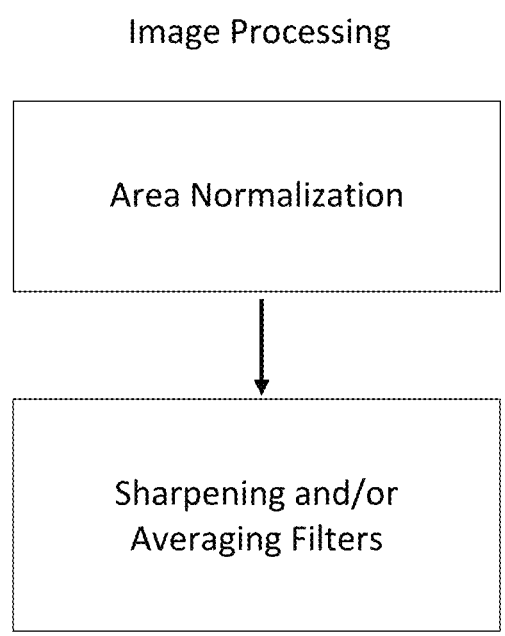

FIG. 1B shows further details of the operation of the DNNs used for segmentation. Each chromosome image of a cell can be area-normalized to compensate for chromosome size variations between individual cells. Two separate DNNs can be used. The first classifies each pixel of the metaphase cell image as belonging to either a background or artefact area, a single chromosome area, a chromosome overlap area, or a chromosome contour. The output of the first DNN is a contour map of the metaphase cell or a portion thereof, in which the individual contours of objects, including single chromosomes and possibly other objects in the field of view. A second DNN can optionally further process the output of the first to classify the identified object as corresponding to debris, a debris cluster possibly including one or more chromosomes, a single chromosome, a chromosome cluster, or two or more overlapping chromosomes. FIG. 1C shows an overview of the segmentation process using first and second DNNs together with optional image processing. FIG. 1D illustrates certain image processing steps which are described below.

Before the classification is performed, the chromosome classes and the sex of the cell are unknown. For human cells, as the X chromosome is much larger than the Y chromosome, using the total or mean area of the entire cell for the normalization would introduce a systematic chromosome scaling error between male and female cells. To avoid this, the areas of all chromosomes can be sorted and the sum of the largest areas is computed which excludes the X chromosome. For example, the 9 largest chromosomes can be summed, as the X chromosome is number 13 in the area sorted chromosome order and will be excluded. The area scaling factor for all chromosomes of the cell can then be computed as the ratio of a pre-determined constant value, and the sum of the largest (e.g., 10 largest) chromosome areas.

Next, optional sharpening and/or averaging filters can be applied. The background of each chromosome image can be extended with white pixels resulting in chromosome images ("tiles") of, for example, 136×136 pixel size. These tiles serve as input for a deep convolutional neuronal net (DNN) that predicts both the class of the chromosome as well as the rotation angle that is required to correctly align the chromosome in the final karyogram.

Figure 2A:
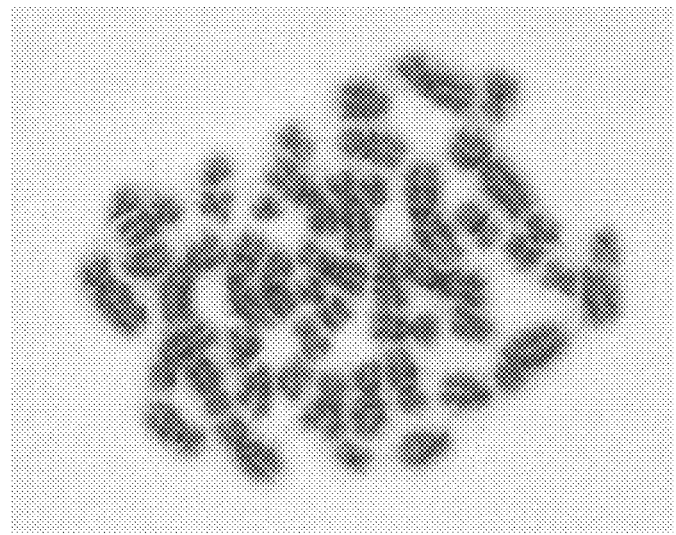
FIGS. 2A-2D show chromosome images from a metaphase cell and segmentation thereof.
Figure 2B:
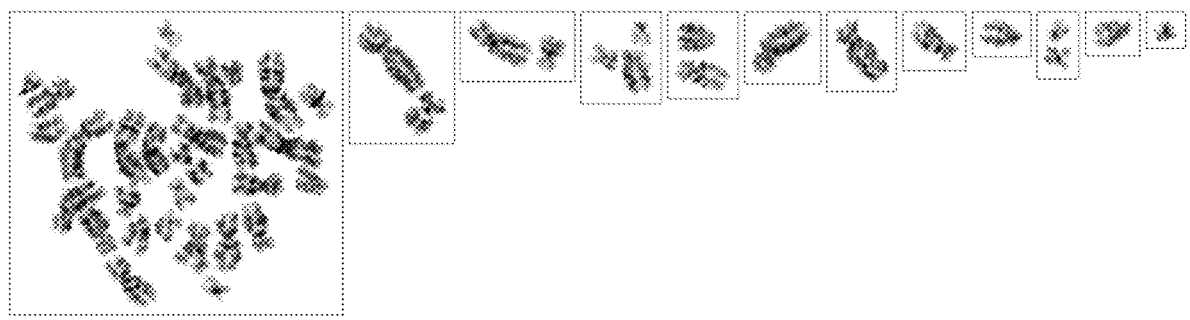
Figure 2C:
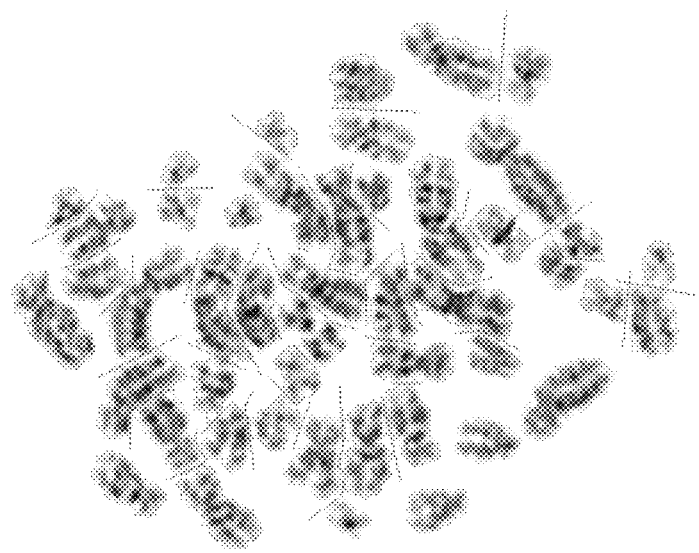
Figure 2D:
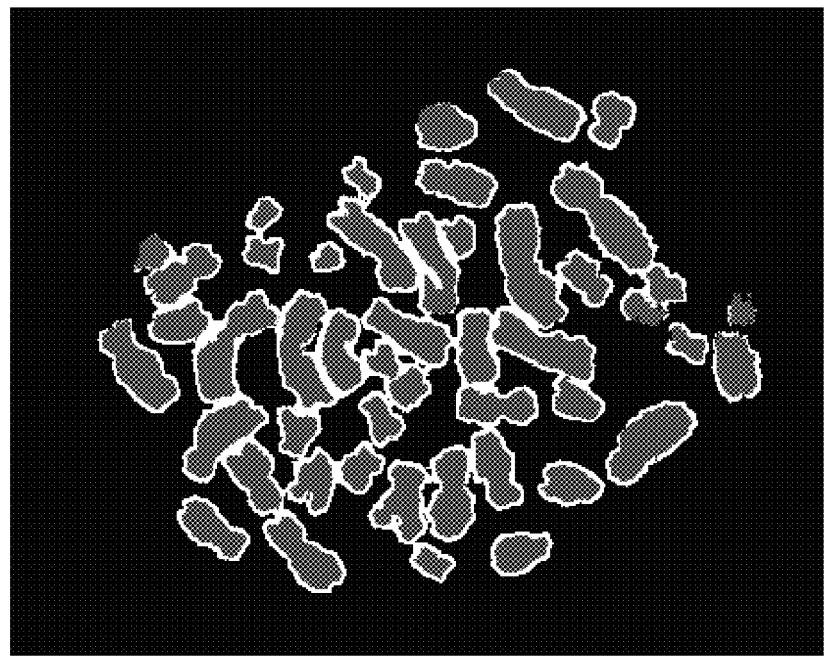
Figure 3A:
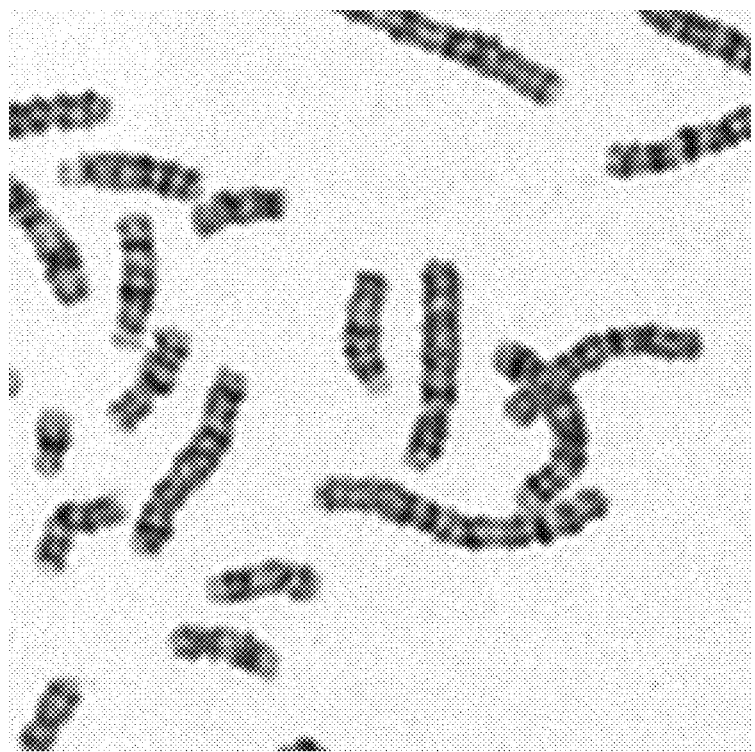
FIGS. 3A-3B show application of a second DNN for object classification.
Figure 3B:
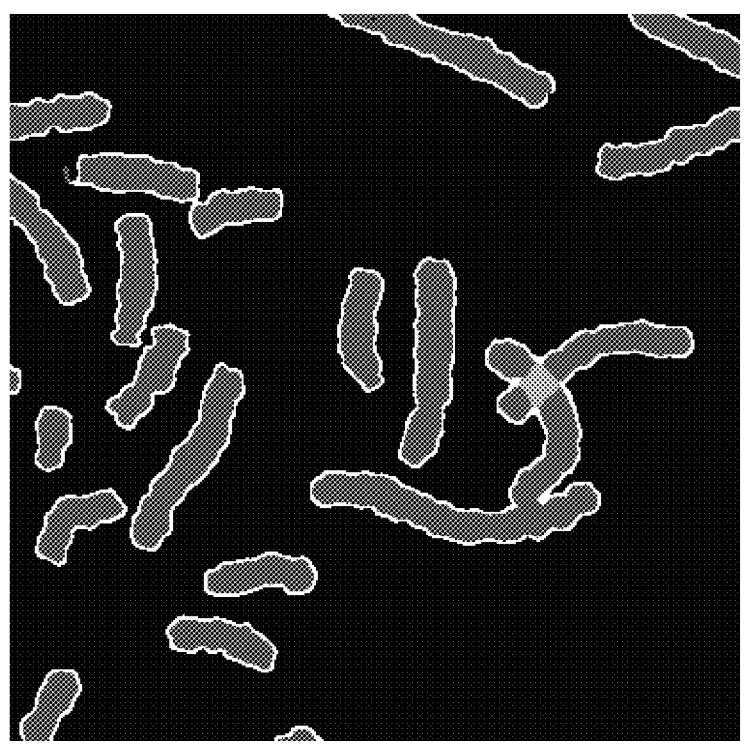

Segmentation of chromosomes can be time consuming, particularly if inhomogenous image background is present. Finding a threshold that separates the chromosomes is often impossible. In such a situation the number of interactive separation steps can be significant. FIGS. 2A-2D show a typical example of a bone marrow metaphase cell. FIG. 2A shows the raw image of the cell. FIG. 2B shows the cell after threshold-based segmentation. FIG. 2C chows the results of an interactive chromosome separation which required 39 interactions. In contrast, FIG. 2D shows the result of a DNN-based segmentation, which more fully identifies the individual boundaries of the set of chromosomes.

The DNNs for the segmentation of chromosomes must be trained with suitable images. Training of the first DNN utilizes pairs of images, in which the first image shows the original metaphase cell as captured by the camera, and the second image is a target map in which each pixel is labelled depending on if it belongs to background/artefact area, chromosome area, overlapping area or the contour of a chromosome. Using these pairs, a DNN can be trained to learn mapping from the original image to the target map. One such DNN architecture was inspired by U-Net (doi.org/10.1007/978-3-319-24574-4_28) with additional short-cut connections within the encoder and decoder. In addition, various image augmentations were used, including rotation and the addition of random noise.

Table 1 below shows a comparison of the number of interactions necessary without (3rd column) and after employing DNN-based segmentation (4th column). The mean number of interaction was reduced from 14.7 to 0.9 per cell, corresponding to a reduction of interactive steps by a factor of 16.

TABLE 1

Comparison of user intervention vs. DNN-based segmentation.

| Cell No | Cell Name | No of Manual Separations | No of interactions after DNN based separation |
| --- | --- | --- | --- |
| 1 | 1900001KB1~A.054 | 41 | 0 |
| 2 | 1900001KI1~A.081 | 16 | 1 |
| 3 | 1900009KF1~A.009 | 15 | 1 |
| 4 | 1900009KI1~A.068 | 11 | 1 |
| 5 | 1900009KM1~A.012 | 8 | 1 |
| 6 | 1900009KN3~A.069 | 17 | 1 |
| 7 | 1900016KC2~A.001 | 2 | 0 |
| 8 | 1900016KE2~A.029 | 0 | 0 |
| 9 | 1900016KN2~A.005 | 13 | 4 |
| 10 | 1900025BC1~A.003 | 17 | 2 |
| 11 | 1900025BE1~A.006 | 13 | 0 |
| 12 | 1900025BE1~A.036 | 0 | 0 |
| 13 | 1900025BE1~A.089 | 5 | 0 |
| 14 | 1900029KA1~A.059 | 14 | 0 |
| 15 | 1900029KC1~A.030 | 22 | 1 |
| 16 | 1900029KE1~A.004 | 4 | 0 |
| 17 | 1900032KB2~A.030 | 27 | 1 |
| 18 | 1900032KC1~A.072 | 19 | 1 |
| 19 | 1900032KE1~A.016 | 26 | 1 |
| 20 | 1900032KE1~A.086 | 23 | 3 |
| Mean | | 14.7 | 0.9 |

For karyotype analysis, the digital image of a metaphase cell can be thresholded to separate the chromosomes from the background. Next, touching and overlapping chromosomes may need to be separated. Automated and partly automated tools in the karyotyping software IKAROS support the user during these steps. Bone marrow derived chromosomes are usually quite short so that many metaphase cells will not require this initial pre-processing step. Once the chromosomes are available as individual objects, they are area-normalized as described before and fed into the DNN classification process, which then provide the karyotype and present it to the user for final check and correction.

An intermediate step in the workflow automation is the decision whether an already separated object is an individual chromosome, a cluster of chromosomes, an artefact or a cluster that includes chromosomes and artefacts. The inventors performed transfer learning of a VGG16-DNN (arxiv.org/abs/1409.1556) to generate a DNN that can perform this decision. During training, various image augmentations were used, including image flipping and the addition of random noise.

A DNN was trained to classify objects into 5 different classes:
1. Debris
2. Debris Cluster (Cluster of one or multiple chromosomes und debris)
3. Single Chromosome
4. Chromosome Cluster
5. Chromosome Overlap Use of the trained DNN yielded an overall accuracy of 98.3%. A total of 60059 objects were analyzed, of which 59022 were correctly classified.

Chromosome segmentation produces a collection of separated chromosome images, preferably having equal pixel number and consistent aspect ratio. For example, chromosome images of 136×136 pixels can be used, but other sizes can be used as long as sufficient resolution is provided. These chromosome tiles serve as input for the chromosome classifying DNN, which can be trained for the cell type, staining method, species, sex, and/or pathological or genetic condition under consideration, including the possible presence of aberrant chromosomes, such as partial chromosomes, translocations, deletions, inversions, and the like.

Figure 1E:
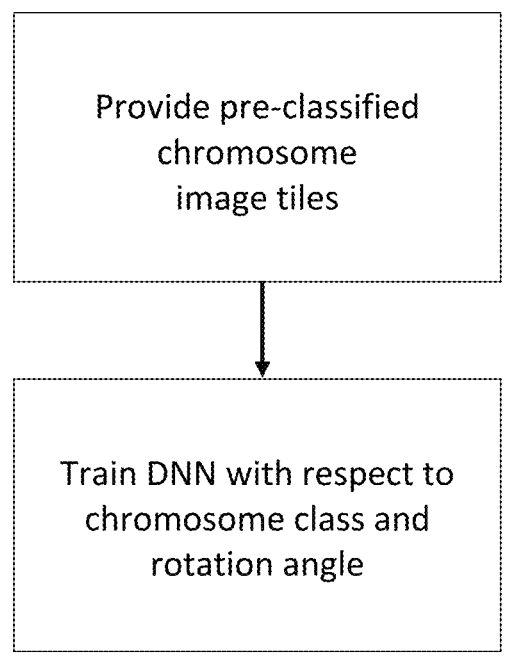
Figure 1F:
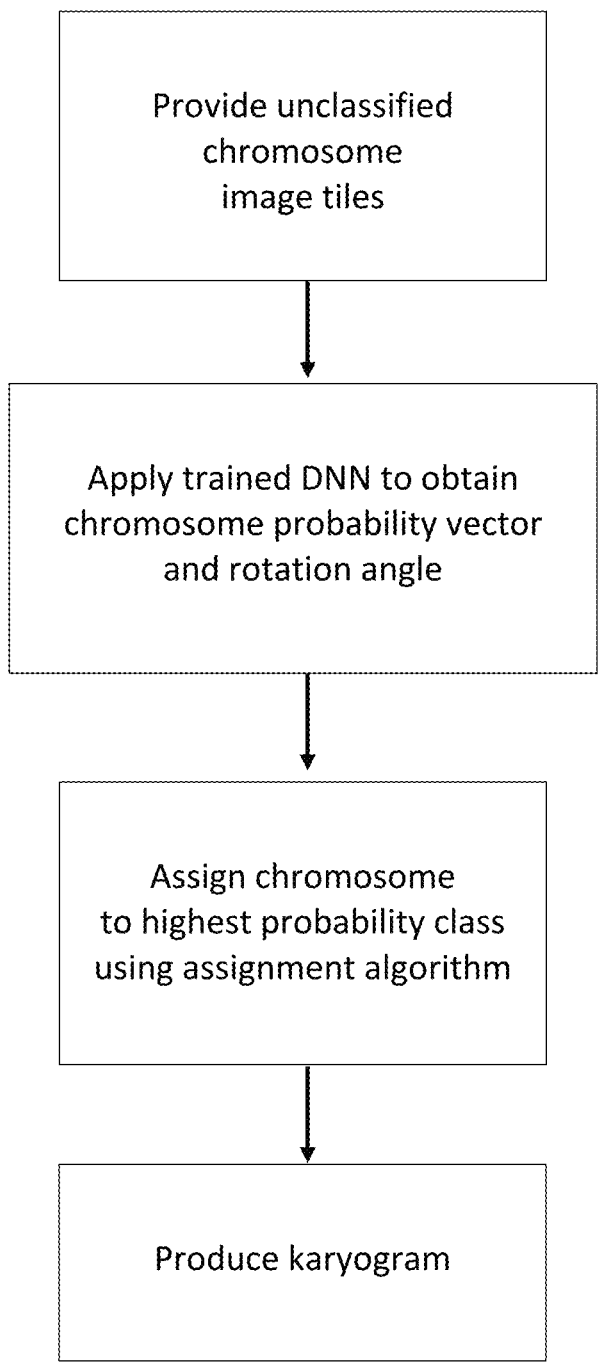

FIG. 1E shows an overview of a process of training a DNN classifier to identify chromosome classes. FIG. 1F shows an overview of a process of using a pre-trained classifier DNN to classify individual chromosome images, and finally to produce a karyotype or karyogram.

Training of the classifier DNN relies on a large number of pre-classified ("tagged") images. As the human genome comprises 23 (female) or 24 (male) different chromosome classes, a sufficient number of images representing chromosomes of all 24 classes are needed. Typically, several thousand training samples per class are required to achieve a sufficiently robust DNN. For example, the training set can include at least 1000, at least 2000, at least 5000, at least 10000, at least 50000, or at least 100000 pre-classified chromosome images.

Computer-assisted karyotyping systems have been used in routine chromosome analysis for the last 3 decades. Consequently, large amounts of pre-classified chromosome images have been generated and archived. Data generated with the IKAROS karyotyping system by MetaSystems Hard and Software GmbH are particularly suited as input to DNN training. Individual chromosome images can be extracted from the IKAROS files along with their tag and class information and can be fed into the training environment.

To extract and condense image information, the DNN can make use of repeating blocks of (3×3) convolutions, concatenation, dropout, (1×1) "net-in-net" convolutions, and average pooling. In order to simultaneously predict chromosome number and rotation angle, the CNN has two distinct final dense layers with, for example, 24 and 360 neurons, respectively. For all chromosomes of the predicted cell, chromosome classes (i.e., chromosome numbers) are hierarchically assigned to chromosomes with the highest respective probability. That is, the DNN outputs a vector of probabilities for each chromosome (24 probabilities for each chromosome). When the probability vectors for all chromosomes of one cell are obtained, the chromosome numbers are assigned according to the highest probabilities and taking into account that only two chromosomes of each class/number should exist.

The DNN returns for each object a rotational angle and a probability vector of dimension N, with N being the number of chromosome classes (24 in a normal human karyogram: autosomes 1 through 22, sex chromosomes X and Y). The following algorithm can be used to then make the final assignment of chromosome class based on the probability vector output of the classifier.

$P_{i,j}$ is the probability matrix resulting from the DNN classification, i is the object index, and j is the class index. $N_j$ are the class counts; $j=1 \ldots 23$, which are initialized to zero. $N_{23}$ is the combined class count of the sex chromosomes (classes 23 and 24). The steps of performing such an assignment algorithm can be as follows:

1. Find the maximum value of all $P_{i,j}$. If the maximum probability $P_{k,l}$ is less than the minimum assignment probability, reject object k and all remaining objects, and terminate the assignment loop.
2. If the maximum probability $P_{k,l}$ is greater than the minimum assignment probability, assign object k to class l.
3. Then set all class probabilities $P_{k,x}$ of object k to zero.
4. For $l=1 \ldots 22$, increment the class count $N_l$ of class l.
5. For $l=23 \ldots 24$, increment the combined class count of the sex chromosomes $N_{23}$.
6. If the class count of class l reaches 2 ($l=1 \ldots 22$), reset the probabilities $P_{x,l}$ for this class for all objects.
7. If the combined class count of the sex chromosomes $N_{23}$ reaches 2, reset the probabilities $P_{x,23}$ and $P_{x,24}$ for all objects.
8. If there are still unassigned chromosomes, go to step 1 to continue the assignment loop.

This assignment method results in a significantly lower classification error rate (2.6% error rate for a test data set of 506 cells, containing 23,276 chromosomes) than the more straightforward method of starting with chromosome 1, looking for the 2 objects with the highest probabilities $P_{i,1}$, then looking for the 2 objects with the highest probabilities $P_{i,2}$, and so on (3.49% error rate), thus reducing the number of interactive corrections by 25%.

Classification results were obtained by applying the pre-trained DNN to an independent set of chromosome images that was not used for DNN training. Pre-processing (e.g., image processing) steps described above may improve the results, but are optional and can be omitted.

The present technology can utilize a DNN with two distinct output layers, one for chromosome number and one for rotation angle. Compared to conventional chromosome classification based on selected extracted features, the DNN based classification provided an improvement of more than 3-fold for both the class assignment and correct orientation of the chromosomes for bone marrow preparations (Table 2) and an improvement of about 10-fold for blood preparations (Table 3). This corresponds to a very substantial time gain in the diagnostic workflow due to a significant reduction of interactive corrections.

TABLE 2

Comparison of conventional banding classifier ("Old") and DNN based approach, applied to chromosomes from bone marrow preparations.

|  | Old | DNN | Fold Reduction |
|---|---|---|---|
| N Classification Errors per Cell: | 29.7 | 8.8 | 3.4 |
| N Orientation Errors per Cell: | 13.7 | 4.5 | 3.1 |

TABLE 3

Comparison of conventional banding classifier ("Old") and DNN based approach, applied on chromosomes from blood preparations.

|  | Old | DNN | Fold Reduction |
|---|---|---|---|
| N Classification Errors per Cell: | 13.2 | 1.3 | 10.5 |
| N Orientation Errors per Cell: | 7.9 | 0.9 | 9.0 |

Table 4 shows the confusion matrix of the DNN classifier for the test data set, the rows correspond to the correct chromosome class, the columns to the automatic chromosome class determined by the DNN classifier. The numbers on the diagonal of the confusion matrix represent correct classifications (since predicted chromosome number=true chromosome number) and are not shown here (they have been set to zero) for the sake of clarity, as this confusion matrix is presented to explain the most common misclassifications. Numbers that do not lie on the diagonal are misclassifications. If they lie close to the diagonal it means that chromosomes were misclassified into neighboring classes. The number 147 in row 4 column 5 for instance means that 147 number 4 chromosomes (out of the total of 962 number 4 chromosomes) were misclassified as number 5 chromosomes. Pairs of classes for which at least one value is 50 or above are shown with bold and italics in the table. These were the most frequent errors, and they correspond to the following chromosome commutations: 4↔5, 7↔X, 8↔10, 9↔10, 9↔X, 13↔14, 14↔15, 17↔18, 9↔20, 19↔22, 21↔22. The training data basis can be expanded by collecting additional karyogram files from the archives of contributing cytogenetic labs, which will allow the reliability of the DNN to be further increased without the need for curating the training data, which is a crucial bottleneck in most DNN training situations.

The DNN's ability to recognize chromosomes depends on the images used for training it. The simplest situation for human cells is a DNN that recognizes the 22 autosomes and 2 sex chromosomes (X and Y). Such a DNN also will allow detection of numerical aberrations like a trisomy, which will result in three chromosomes (instead of one or two in the normal karyogram) having a high probability of belonging to a particular class.

Chromosomal abnormalities involving structural rearrangements of chromosomes from different classes are regularly encountered in leukemia diagnostics. The DNN can easily be trained to also recognize common rearrangements like the BCR-ABL translocation resulting in the so called "Philadelphia Chromosome". To this end a sufficient number of example images of this rearrangement need to be included in the training set, and the number of classes needs to be extended accordingly.

In order to automatically detect some of the most important structural chromosome aberrations, a DNN was trained that contained additional chromosome classes representing the aberrant chromosomes. Training of the DNN was performed as described above. The training data set comprised a total of 54,634 karyograms, as shown in Table 5.

TABLE 5

Training set for aberrant chromosome detection.

| No | aberration | karyograms |
|---|---|---|
| 1 | t(9;22)(q34;q11) | 12,766 |
| 2 | t(15;17)(q24;q21) | 5,010 |
| 3 | t(11;14)(q13;q32) | 1,845 |
| 4 | der(1;7)(q10;p10) | 2,377 |
| 5 | inv(3)(q21q26) | 3,838 |
| 6 | inv(16)(p13q22) | 5,907 |
| 7 | t(9;11)(p21;q23) | 2,744 |
| 8 | t(8;21)(q22;q22) | 5,487 |

TABLE 4

Confusion matrix of DNN classifier

|  | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|
| 1 | 0 | 8 | 2 | 0 | 0 | 0 | 0 | 0 | 0 | 0 | 0 | 0 | 0 | 0 | 0 | 0 | 0 | 0 | 0 | 0 | 0 | 0 | 0 | 0 |
| 2 | 4 | 0 | 4 | 1 | 0 | 1 | 0 | 0 | 0 | 0 | 0 | 0 | 0 | 0 | 0 | 0 | 0 | 0 | 0 | 0 | 1 | 0 | 0 |
| 3 | 3 | 0 | 0 | 4 | 2 | 4 | 7 | 0 | 0 | 1 | 0 | 0 | 0 | 0 | 0 | 0 | 0 | 0 | 0 | 0 | 0 | 0 | 0 | 0 |
| 4 | 1 | 1 | 3 | 0 | *147* | 10 | 2 | 2 | 3 | 1 | 0 | 1 | 0 | 0 | 0 | 1 | 0 | 0 | 0 | 0 | 1 | 1 | 0 | 0 |
| 5 | 1 | 0 | 2 | *139* | 0 | 16 | 7 | 7 | 1 | 2 | 0 | 0 | 0 | 0 | 0 | 1 | 1 | 1 | 2 | 0 | 1 | 1 | 0 |
| 6 | 0 | 1 | 3 | 17 | 18 | 0 | 48 | 8 | 4 | 5 | 1 | 0 | 0 | 0 | 0 | 0 | 2 | 0 | 1 | 0 | 1 | 0 | 17 | 0 |
| 7 | 0 | 0 | 2 | 1 | 0 | 31 | 0 | 12 | 48 | 7 | 5 | 2 | 0 | 0 | 0 | 1 | 2 | 0 | 1 | 0 | 1 | 5 | *133* | 0 |
| 8 | 0 | 0 | 0 | 0 | 7 | 12 | 12 | 0 | 43 | *126* | 3 | 37 | 2 | 0 | 0 | 3 | 0 | 0 | 1 | 0 | 1 | 2 | 42 | 0 |
| 9 | 0 | 0 | 0 | 0 | 1 | 9 | 47 | 37 | 0 | *46* | 43 | 18 | 1 | 3 | 1 | 4 | 1 | 1 | 2 | 1 | 2 | 1 | *63* | 0 |
| 10 | 1 | 0 | 0 | 1 | 1 | 6 | 3 | *138* | 57 | 0 | 1 | 43 | 2 | 3 | 4 | 1 | 1 | 0 | 1 | 0 | 0 | 0 | 12 | 0 |
| 11 | 0 | 1 | 1 | 0 | 1 | 5 | 3 | 1 | 32 | 5 | 0 | 8 | 3 | 0 | 0 | 0 | 1 | 0 | 0 | 1 | 1 | 3 | 0 |
| 12 | 0 | 0 | 2 | 0 | 0 | 1 | 3 | 43 | 12 | 43 | 2 | 0 | 8 | 7 | 1 | 2 | 0 | 0 | 1 | 1 | 0 | 0 | 1 | 0 |
| 13 | 0 | 0 | 0 | 2 | 0 | 0 | 1 | 3 | 1 | 3 | 0 | 4 | 0 | *95* | 47 | 4 | 4 | 9 | 1 | 1 | 0 | 2 | 0 | 0 |
| 14 | 0 | 0 | 0 | 1 | 0 | 1 | 0 | 1 | 3 | 6 | 3 | 4 | *97* | 0 | *232* | 4 | 9 | 18 | 7 | 0 | 3 | 3 | 0 | 1 |
| 15 | 0 | 0 | 0 | 0 | 0 | 0 | 1 | 3 | 4 | 4 | 1 | 0 | 45 | *236* | 0 | 6 | 13 | 32 | 1 | 1 | 0 | 0 | 0 | 0 |
| 16 | 0 | 0 | 0 | 0 | 0 | 0 | 0 | 0 | 2 | 1 | 0 | 1 | 3 | 9 | 4 | 0 | 9 | 22 | 8 | 7 | 0 | 1 | 0 | 0 |
| 17 | 0 | 0 | 0 | 0 | 0 | 0 | 1 | 0 | 0 | 1 | 1 | 1 | 2 | 11 | 11 | 11 | 0 | *87* | 4 | 12 | 1 | 2 | 0 | 9 |
| 18 | 0 | 0 | 0 | 0 | 0 | 0 | 0 | 0 | 2 | 1 | 0 | 1 | 11 | 26 | 44 | 9 | *80* | 0 | 4 | 3 | 1 | 1 | 0 | 19 |
| 19 | 0 | 0 | 0 | 3 | 0 | 1 | 4 | 1 | 2 | 0 | 0 | 0 | 0 | 0 | 1 | 3 | 3 | 0 | *79* | 28 | *62* | 0 | 8 |
| 20 | 0 | 0 | 0 | 0 | 0 | 0 | 2 | 0 | 0 | 1 | 0 | 0 | 0 | 1 | 2 | 10 | 11 | 8 | *74* | 0 | 4 | 1 | 0 | 10 |
| 21 | 0 | 0 | 0 | 1 | 0 | 2 | 3 | 1 | 3 | 0 | 0 | 0 | 2 | 1 | 0 | 1 | 3 | 6 | 29 | 4 | 0 | *97* | 0 | 35 |
| 22 | 0 | 0 | 0 | 0 | 0 | 2 | 7 | 5 | 2 | 0 | 0 | 1 | 0 | 1 | 1 | 6 | 5 | 3 | *47* | 7 | *106* | 0 | 0 | 23 |
| 23 | 0 | 0 | 2 | 2 | 4 | 21 | *93* | 22 | *59* | 17 | 6 | 4 | 1 | 0 | 0 | 1 | 3 | 0 | 2 | 1 | 3 | 7 | 0 | 0 |
| 24 | 0 | 0 | 0 | 2 | 1 | 4 | 7 | 7 | 3 | 5 | 0 | 2 | 0 | 0 | 0 | 1 | 7 | 11 | 9 | 7 | 35 | 28 | 0 | 0 |

TABLE 5-continued

Training set for aberrant chromosome detection.

| No | aberration | karyograms |
|---|---|---|
| 9 | del(5)(q14q34) | 10,497 |
| 10 | del(5)(q21q34) | 4,163 |
| | total | 54,634 |

Table 6 below shows the aberrant chromosomes included in the training set (for aberrations involving two chromosomes, two derivative chromosomes were included).

TABLE 6

Chromosomes used to train classifier for aberrant chromosomes.

| No | aberrant chromosome | abbreviation | class |
|---|---|---|---|
| 1A | der(9)t(9;22)(q34;q11) | der9t9;22 | 25 |
| 1B | der(22)t(9;22)(q34;q11) | der22t9;22 | 26 |
| 2A | der(15)t(15;17)(q24;q21) | der15t15; 17 | 27 |
| 2B | der(17)t(15;17)(q24;q21) | der17t15;17 | 28 |
| 3A | der(11)t(11;14)(q13;q32) | der11t11;14 | 29 |
| 3B | der(14)t(11;14)(q13;q32) | der14t11;14 | 30 |
| 4 | der(7)der(1;7)(q10;p10) | der7der1;7 | 31 |
| 5 | inv(3)(q21q26) | inv3q21q26 | 32 |
| 6 | inv(16)(p13q22) | inv16p13q22 | 33 |
| 7A | der(9)t(9;11)(p21;q23) | der9t9;11 | 34 |
| 7B | der(11)t(9;11)(p21;q23) | der11t9;11 | 35 |
| 8A | der(8)t(8;21)(q22;q22) | der8t8;21 | 36 |
| 8B | der(21)t(8;21)(q22;q22) | der21t8;21 | 37 |
| 9 | del(5)(q14q34) | del5q14q34 | 38 |
| 10 | del(5)(q21q34) | del5q21q34 | 39 |

Results are shown in Table 7 below for a test set of unclassified chromosomes, including 2 cells each for each of the 10 aberrations shown in Table 5. Comparison was made of DNNs trained using two different training data sets.

TABLE 7

Results for classification of aberrant chromosomes

| DNN | training data set | | | |
|---|---|---|---|---|
| Aberr39-A | all aberrant plus about the same number of normal chromosomes | | | |
| Aberr39-B | all aberrant chromosomes plus 100,000 normal karyograms | | | |

| | | Aberr39-A | | Aberr-39B | |
|---|---|---|---|---|---|
| | | der | der2 | der | der2 |
| aberration | cell | detected? | detected? | detected? | detected? |
| 1 | 1 | + | + | + | + |
| 1 | 2 | − | + | + | + |
| 2 | 1 | − | − | − | + |
| 2 | 2 | − | + | + | + |
| 3 | 1 | + | + | + | + |
| 3 | 2 | − | + | + | + |
| 4 | 1 | + | | + | |
| 4 | 2 | + | | + | |
| 5 | 1 | − | | − | |
| 5 | 2 | − | | + | |
| 6 | 1 | − | | + | |
| 6 | 2 | + | | + | |
| 7 | 1 | − | − | − | − |
| 7 | 2 | − | + | − | + |
| 8 | 1 | + | + | + | + |
| 8 | 2 | + | + | + | + |
| 9 | 1 | + | | + | |
| 9 | 2 | + | | + | |
| 10 | 1 | + | | − | |
| 10 | 2 | + | | − | |

TABLE 7-continued

Results for classification of aberrant chromosomes

| | Aberr39-A | Aberr39-B |
|---|---|---|
| aberrations detected | 15 | 16 |
| aberrations not detected | 5 | 4 |
| total | 20 | 20 |

15 (DNN Aberr39-A) and 16 (DNN Aberr39-A) out of 20 aberrations were correctly recovered by the DNN.

Figure 4A:
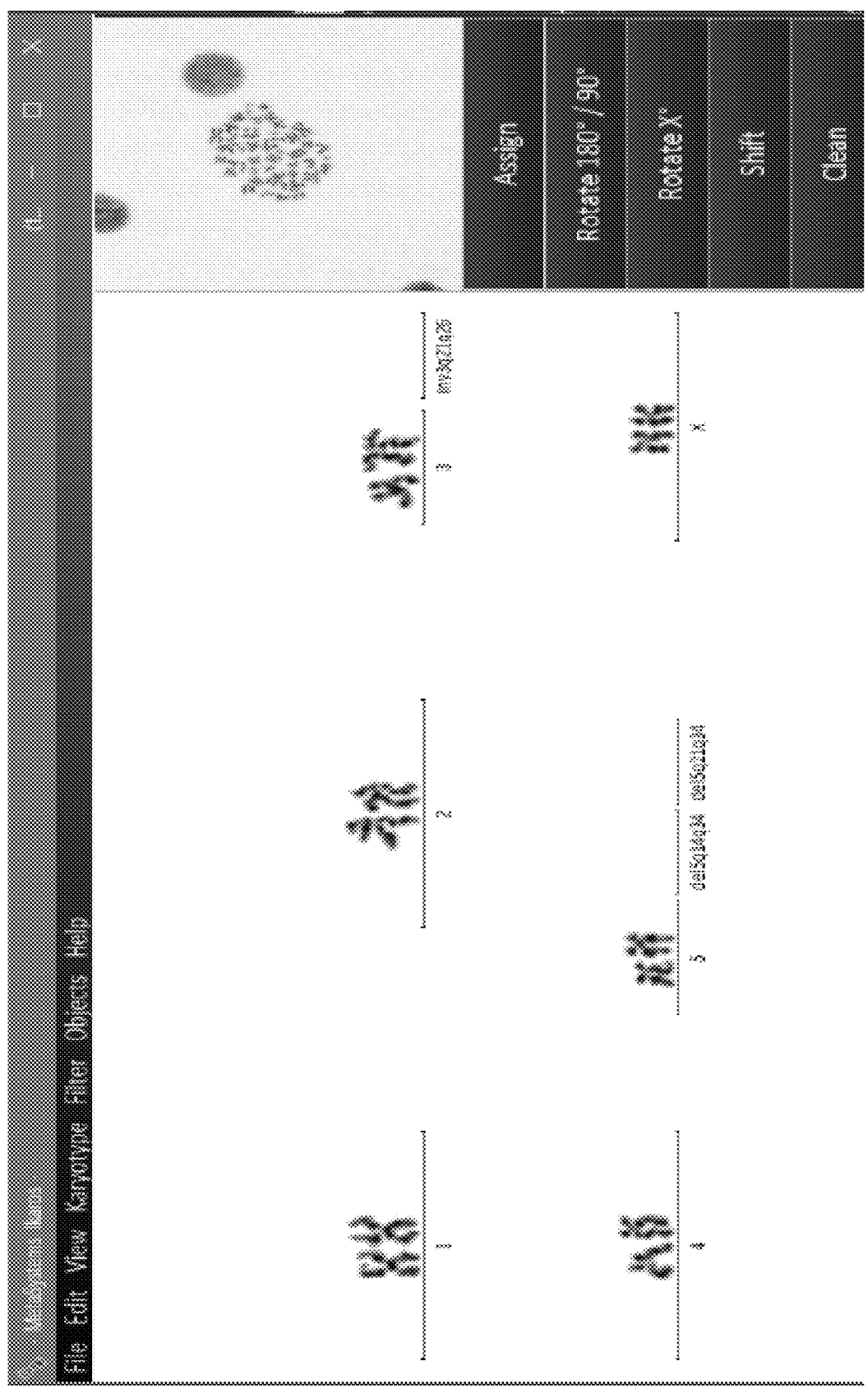
FIGS. 4A-4B show karyograms containing chromosome aberration classes identified by a trained chromosome classifying DNN.
Figure 4B:
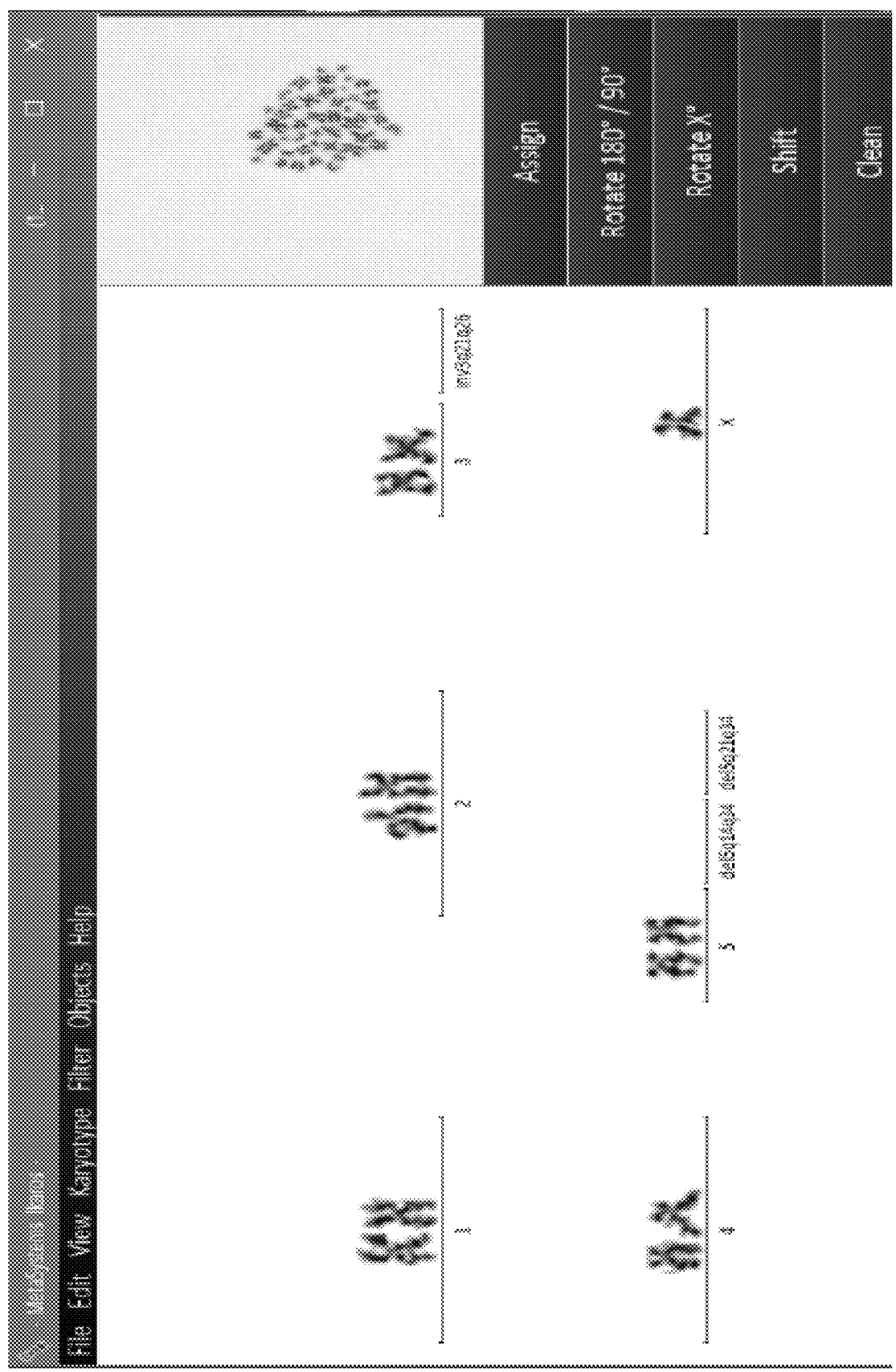
Figure 4B:
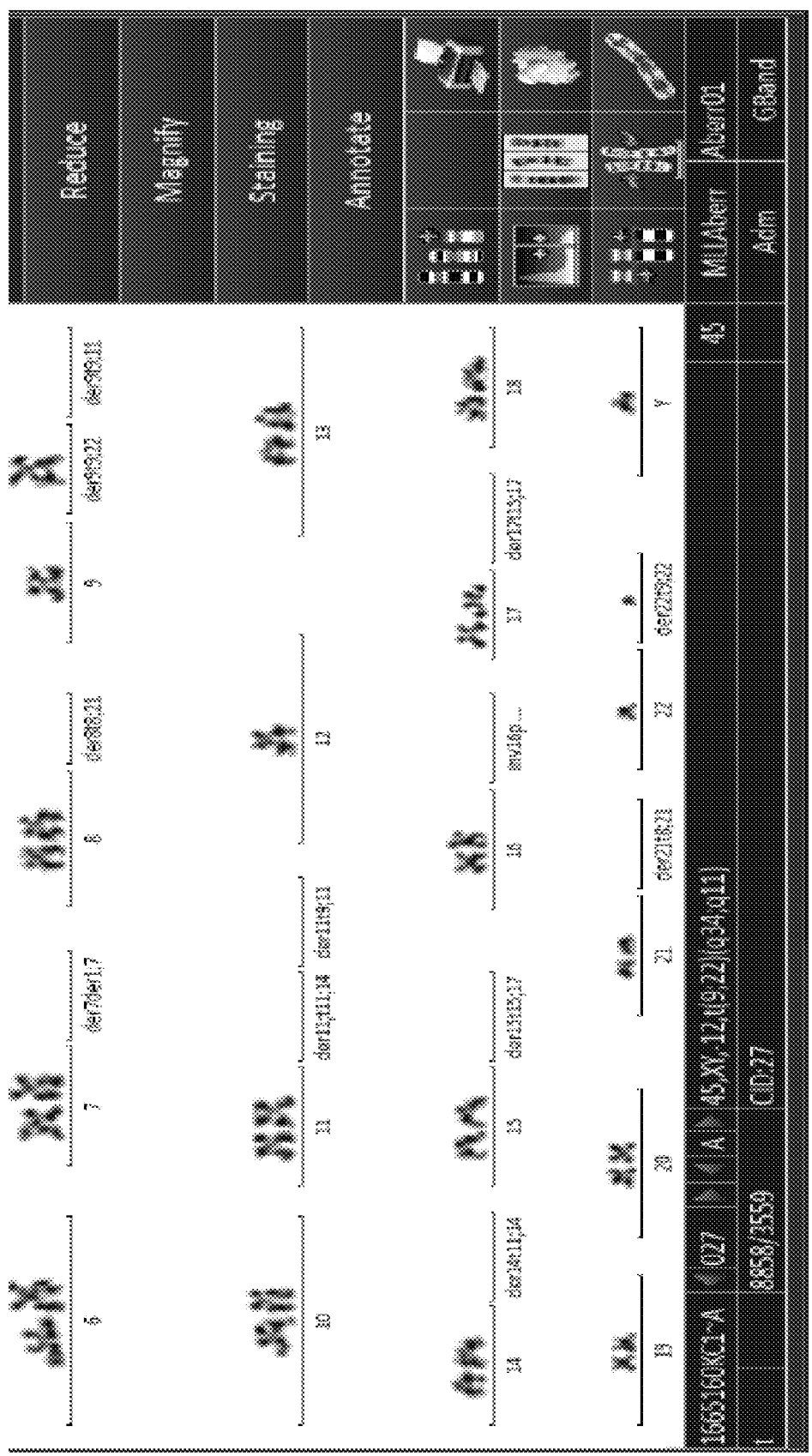

FIGS. 4A and 4B show examples of karyograms that reveal detection of aberrant chromosomes. FIG. 4A shows a karyogram with the aberration t(8; 21)(q22; q22). FIG. 4B shows the BCR-ABL aberration t(9; 22)(q34; q11) resulting in a Philadelphia Chromosome.

The methods described herein can be implemented in any suitable computing system. The computing system can be implemented as or can include a computer device that includes a combination of hardware, software, and firmware that allows the computing device to run an applications layer or otherwise perform various processing tasks. Computing devices can include without limitation personal computers, work stations, servers, laptop computers, tablet computers, mobile devices, wireless devices, smartphones, wearable devices, embedded devices, microprocessor-based devices, microcontroller-based devices, programmable consumer electronics, mini-computers, main frame computers, and the like and combinations thereof.

Processing tasks can be carried out by one or more processors. Various types of processing technology can be used including a single processor or multiple processors, a central processing unit (CPU), multicore processors, parallel processors, or distributed processors. Additional specialized processing resources such as graphics (e.g., a graphics processing unit or GPU), video, multimedia, or mathematical processing capabilities can be provided to perform certain processing tasks. Processing tasks can be implemented with computer-executable instructions, such as application programs or other program modules, executed by the computing device. Application programs and program modules can include routines, subroutines, programs, scripts, drivers, objects, components, data structures, and the like that perform particular tasks or operate on data.

Processors can include one or more logic devices, such as small-scale integrated circuits, programmable logic arrays, programmable logic devices, masked-programmed gate arrays, field programmable gate arrays (FPGAs), application specific integrated circuits (ASICs), and complex programmable logic devices (CPLDs). Logic devices can include, without limitation, arithmetic logic blocks and operators, registers, finite state machines, multiplexers, accumulators, comparators, counters, look-up tables, gates, latches, flip-flops, input and output ports, carry in and carry out ports, and parity generators, and interconnection resources for logic blocks, logic units and logic cells.

The computing device includes memory or storage, which can be accessed by a system bus or in any other manner. Memory can store control logic, instructions, and/or data. Memory can include transitory memory, such as cache memory, random access memory (RAM), static random access memory (SRAM), main memory, dynamic random access memory (DRAM), block random access memory (BRAM), and memristor memory cells. Memory can include storage for firmware or microcode, such as programmable read only memory (PROM) and erasable programmable read only memory (EPROM). Memory can include non-transitory or nonvolatile or persistent memory such as read only memory (ROM), one time programmable non-volatile memory (OTPNVM), hard disk drives, optical storage devices, compact disc drives, flash drives, floppy disk drives, magnetic tape drives, memory chips, and memristor memory cells. Non-transitory memory can be provided on a removable storage device. A computer-readable medium can include any physical medium that is capable of encoding instructions and/or storing data that can be subsequently used by a processor to implement embodiments of the systems and methods described herein. Physical media can include floppy discs, optical discs, CDs, mini-CDs, DVDs, HD-DVDs, Blu-ray discs, hard drives, tape drives, flash memory, or memory chips. Any other type of tangible, non-transitory storage that can provide instructions and/or data to a processor can be used in the systems and methods described herein.

The computing device can include one or more input/output interfaces for connecting input and output devices to various other components of the computing device. Input and output devices can include, without limitation, keyboards, mice, joysticks, microphones, cameras, webcams, displays, touchscreens, monitors, scanners, speakers, and printers. Interfaces can include universal serial bus (USB) ports, serial ports, parallel ports, game ports, and the like.

The computing device can access a network over a network connection that provides the computing device with telecommunications capabilities Network connection enables the computing device to communicate and interact with any combination of remote devices, remote networks, and remote entities via a communications link. The communications link can be any type of communication link including without limitation a wired or wireless link. For example, the network connection can allow the computing device to communicate with remote devices over a network which can be a wired and/or a wireless network, and which can include any combination of intranet, local area networks (LANs), enterprise-wide networks, medium area networks, wide area networks (WANS), virtual private networks (VPNs), the Internet, cellular networks, and the like. Control logic and/or data can be transmitted to and from the computing device via the network connection. The network connection can include a modem, a network interface (such as an Ethernet card), a communication port, a PCMCIA slot and card, or the like to enable transmission to and receipt of data via the communications link. A transceiver can include one or more devices that both transmit and receive signals, whether sharing common circuitry, housing, or a circuit boards, or whether distributed over separated circuitry, housings, or circuit boards, and can include a transmitter-receiver.

The computing device can include a browser and a display that allow a user to browse and view pages or other content served by a web server over the communications link. A web server, sever, and database can be located at the same or at different locations and can be part of the same computing device, different computing devices, or distributed across a network. A data center can be located at a remote location and accessed by the computing device over a network. The computer system can include architecture distributed over one or more networks, such as, for example, a cloud computing architecture. Cloud computing includes without limitation distributed network architectures for providing, for example, software as a service (SaaS).

As used herein, "consisting essentially of" allows the inclusion of materials or steps that do not materially affect the basic and novel characteristics of the claim. Any recitation herein of the term "comprising", particularly in a description of components of a composition or in a description of elements of a device, can be exchanged with the alternative expressions "consisting essentially of" or "consisting of".

REFERENCES

Sharma M, Saha O, Sriraman A, Hebbalaguppe R, Vig L, Karande S, "Crowdsourcing for Chromosome Segmentation and Deep Classification", The IEEE Conference on Computer Vision and Pattern Recognition (CVPR) Workshops, 2017, pp. 34-41

What is claimed is:

1. A method to aid in classifying metaphase chromosomes of a cell, the method comprising the steps of:
    (a) providing a digital image of a metaphase cell;
    (b) segmenting the image into objects, whereby digital images of metaphase chromosomes of the cell are obtained;
    (c) analyzing each chromosome image using a classifying pre-trained deep convolutional neural network (DNN) comprising a first output layer for chromosome classification and a second output layer for chromosome rotation, thereby obtaining for each chromosome (i) a probability vector for use in assigning a class of the chromosome and (ii) a rotation angle of the chromosome in said digital image of the metaphase cell;
    (d) assigning the chromosome image with the highest assignment probability to the class predicted for that probability;
    (e) repeating step (d) with the chromosome image having the next highest assignment probability, until all chromosome images from the image of the metaphase cell have been assigned, with the proviso that once an expected total number of chromosomes for a given class has been reached, assignment probabilities for that class are set to zero or can be recalculated for all remaining chromosome images; and
    (f) preparing a karyogram using the classified metaphase chromosome images.

2. The method of claim 1, wherein the probability vectors of all chromosomes in the image of the metaphase cell are represented as a probability matrix.

3. The method of claim 1, wherein all chromosomes of the metaphase cell are represented in the digital image of the metaphase cell.

4. The method of claim 1, wherein chromosome images having an assignment probability below a user-defined threshold are not assigned automatically, but remain unclassified.

5. The method of claim 1, wherein the metaphase cell was pre-treated to reveal one or more nucleic acid sequences or one or more bands or positions on the metaphase chromosomes, and the DNN was pre-trained using the same pre-treatment.

6. The method of claim 5, wherein the pre-treatment comprises performing fluorescence in situ hybridization (FISH), or a variant thereof using non-fluorescent labels.

7. The method of claim 1, wherein the metaphase cell is a eukaryotic cell, such as a cell from a plant, animal, mammal, or human.

8. The method of claim 1, further comprising processing the digital image of the metaphase cell, or the digital image of one or more metaphase chromosomes, using an automated or interactive image processing method.

9. The method of claim 8, wherein the image processing method is selected from the group consisting of convolution, concatenation, dropout, average pooling, thresholding, applying a sharpening or averaging filter, gray level transformation, normalization, area normalization, rotation, flipping, addition of random noise, and threshold based segmentation.

10. The method of claim 1 which detects additional or missing chromosomes of a class.

11. The method of claim 1 which detects structural aberrations or debris.

12. The method of claim 11, wherein the structural aberration is selected from the group consisting of dicentric chromosomes, ring chromosomes, Philadelphia chromosome, and other chromosomal aberrations.

13. The method of claim 12, wherein the structural aberration is selected from the group consisting of translocation t(9; 22)(q34; q11), translocation t(15; 17)(q24; q21), translocation t(11; 14)(q13; q32), derivative der(1; 7)(q10; p10), inversion inv(3)(q21q26), inversion inv(16)(p13q22), translocation t(9:11)(p21; q23), translocation t(8; 21)(q22; q22), deletion del(5)(q14q34), and deletion del(5)(q21q34).

14. The method of claim 1, wherein step (a) comprises analyzing a plurality of images of metaphase cells and rejecting or flagging images of metaphase cells containing overlapping chromosomes.

15. The method of claim 1, wherein step (b) comprises rejecting or flagging images of metaphase cells containing fewer metaphase chromosomes than expected.

16. The method of claim 1, wherein step (b) comprises:
(i) optionally applying one or more image processing steps to the digital image of the metaphase cell;
(ii) segmenting the digital image of the metaphase cell into object images using a pre-trained first segmenting DNN;
(iii) optionally applying one or more image processing steps to the object images obtained from (ii);
(iv) classifying the objects obtained in (ii) or (iii) using a pre-trained second segmenting DNN, thereby identifying objects that comprise metaphase chromosome images; and
(v) preparing digital images of the metaphase chromosomes from the metaphase chromosome images obtained in (iii), wherein the prepared digital images have equal numbers of pixels and equal aspect ratios and are suitable as input for the classifying DNN of step (c).

17. The method of claim 16, wherein the image processing method of step (i) and/or step (iii) is selected from the group consisting of convolution, concatenation, dropout, average pooling, thresholding, applying a sharpening or averaging filter, gray level transformation, normalization, area normalization, rotation, flipping, addition of random noise, and threshold-based segmentation.

18. The method of claim 16, wherein the first segmenting DNN was pre-trained to classify pixels of the digital image of the metaphase cell as background or artefact area, chromosome area, chromosome overlap area, or chromosome contour.

19. The method of claim 18, wherein the second segmenting DNN was pre-trained to classify objects from step (ii) or (iii) as containing debris, debris+chromosome, single chromosome, chromosome cluster, or overlapped chromosomes.

20. The method of claim 16, wherein the second segmenting DNN was pre-trained to classify objects from step (ii) or (iii) as containing debris, debris+chromosome, single chromosome, chromosome cluster, or overlapped chromosomes.

21. The method of claim 1, further comprising, prior to step (a), identifying metaphase cells in a plurality of cells on a microscope slide.

22. A system for automated or semi-automated chromosome classification, the system comprising:
(i) a light microscope with a digital imaging device, wherein the microscope optionally comprises a motorized focus and scanning stage;
(ii) a computer configured to control the motorized microscope and digital imaging device, and to capture images; and
(iii) software configured to perform the method of claim 1.

23. A method of training a deep convolutional neural network (DNN) for use in classifying metaphase chromosomes, the method comprising the steps of:
(a) providing at least 10,000 sets of training images of metaphase chromosomes, the images of each set containing pre-classified images of all metaphase chromosomes from a metaphase cell of a selected cell type;
(b) providing a DNN comprising a first output layer for chromosome classification and a second output layer for determining chromosome rotation, wherein the DNN outputs for each chromosome (i) a probability vector for use in assigning a class of the chromosome and (ii) a rotation angle of the chromosome in the digital image, and wherein the DNN outputs for each image a probability matrix comprising the probability vectors of all chromosomes in the image; and
(c) training the DNN with the plurality of sets of training images of metaphase chromosomes.

24. The method of claim 23, wherein the sets of training images are karyograms, and at least 50,000, or at least 100,000 karyograms are used to train the DNN.

* * * * *